Figure 1:
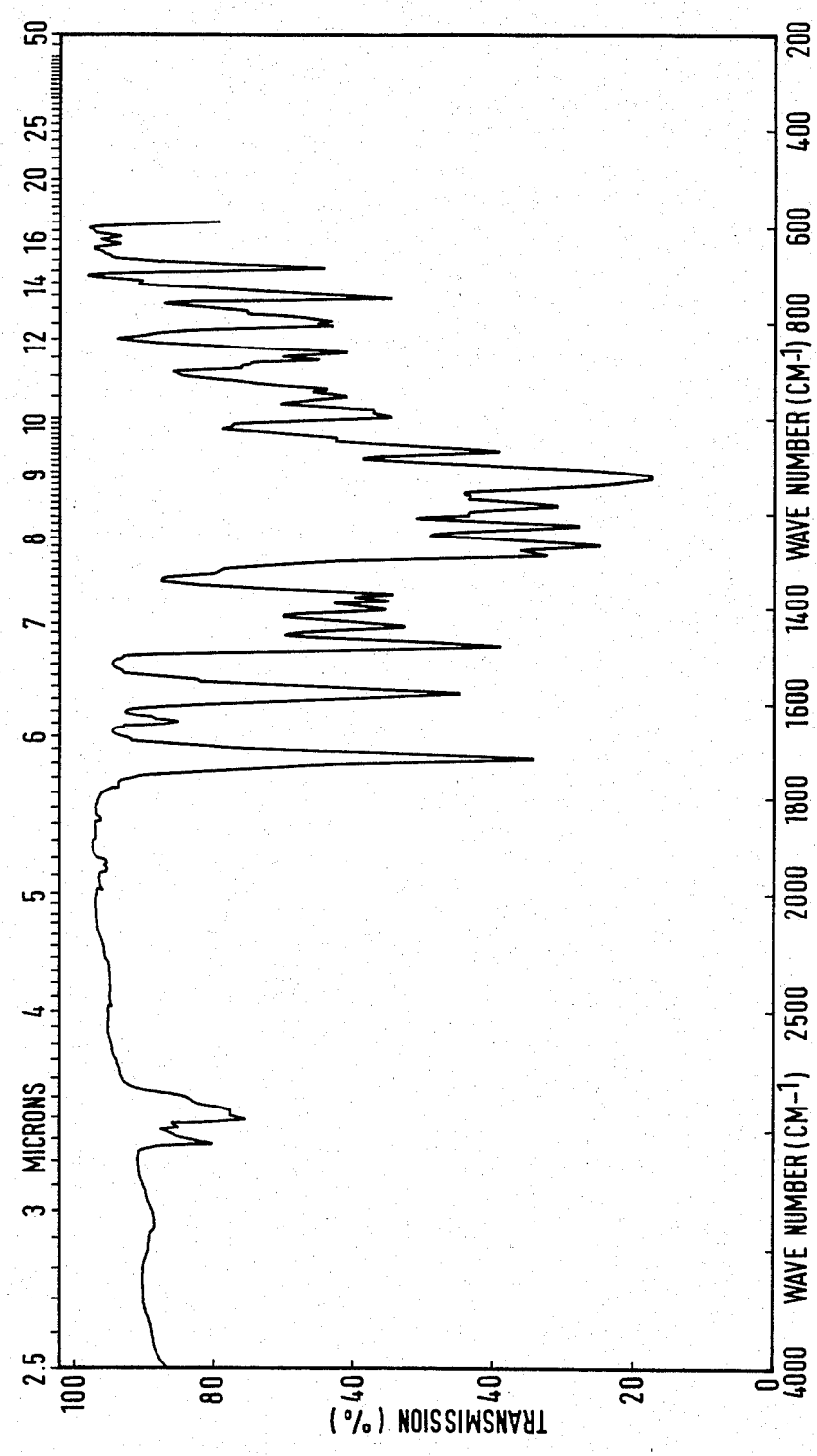

United States Patent [19]

Crosby

[11] Patent Number: 4,510,098

[45] Date of Patent: Apr. 9, 1985

[54] INSECTICIDAL PRODUCT

[75] Inventor: John Crosby, Cheshire, England

[73] Assignee: Imperial Chemical Industries PLC, London, England

[21] Appl. No.: 535,624

[22] Filed: Sep. 26, 1983

[30] Foreign Application Priority Data

Mar. 28, 1983 [GB] United Kingdom ............... 8308507

[51] Int. Cl.³ ........................................... C07C 121/75
[52] U.S. Cl. ................................................ 260/465 D
[58] Field of Search ................................... 260/465 D

[56]  References Cited

U.S. PATENT DOCUMENTS 4,183,948  1/1980  Huff .................................. 424/304
4,308,279  12/1981 Smeltz ............................... 424/304

FOREIGN PATENT DOCUMENTS

A2000764  6/1981  United Kingdom .

OTHER PUBLICATIONS

Pesticide Science, vol. 11, No. 2, 1980, pp. 156–164, Society of Chemical Industry, Bentley et al., "Fluorinated Analogues of Chrysanthemic Acid".

Primary Examiner—Dolph H. Torrence
Attorney, Agent, or Firm—Cushman, Darby & Cushman

[57]  ABSTRACT

A novel crystalline modification of an enantiomeric pair of isomers of the insecticide cyhalothrin having improved handling characteristics.

5 Claims, 3 Drawing Figures

INSECTICIDAL PRODUCT

This invention relates to an insecticidal product and methods of preparing it.

The compound α-cyano-3-phenoxybenzyl cis-3-(Z-2-chloro-3,3,3-trifluoroprop-1-en-1-yl)-2,2-dimethylcyclopropane carboxylate, also known by its common name of cyhalothrin, its preparation and insecticidal use is described inter alia in U.S. Pat. No. 4,183,948. This product is a mixture of four isomers which may be conveniently described as follows:

Isomer A—the ester derived from the (+)-cis-acid and the α-(S)-alcohol.

Isomer B—the ester derived from the (−)-cis-acid and the α-(R)-alcohol.

Isomer C—the ester derived from the (+)-cis-acid and the α-(R)-alcohol.

Isomer D—the ester derived from the (−)-cis-acid and the α-(S)-alcohol.

Cyhalothrin itself contains typically from 40–60% by weight of isomers A and B and 60–40% by weight of isomers C and D and is a viscous liquid at the ambient temperature. It cannot be induced to crystallise by cooling.

Now isomer A and isomer B have identical physical properties, eg. solubility, melting point, etc, differing only in the direction in which they rotate the plane of polarised light, and as such represent a pair of enantiomers. Similarly, isomer C and isomer D represent a second enantiomeric pair.

It is known from P. D. Bentley et al, Pestic. Sci., 11, (2), 156-64 (1980) that Isomer A is the most active insecticide of the four isomers and that isomers B and D were insecticidally inactive in tests against houseflies (*Musca domestica*). Isomer A is in fact about 25 times more active than the known insecticide permethrin in this test, making it one of the most active synthetic insecticides yet reported. Although it would be desirable to use isomer A alone as the active ingredient of insecticidal preparations, this is not easy to achieve in an economical manner because this requires that the acid and alcohol moieties of the isomer be prepared by chiral synthetic techniques and reacted together in a manner which does not change the chirality. Such techniques have not yet been developed to a level where such a synthesis can be carried out in an economic manner without the co-production of unwanted isomeric products which require to be separated using expensive reagents.

A technique has recently been discovered whereby the pair of enantiomers represented by isomer A and isomer B can be readily separated from isomer C and isomer D by physical means not requiring chiral synthesis or chemical resolution, and that insecticidal products of acceptable efficacy can be prepared in an economic manner using the enantiomer pair.

This technique provides a process for obtaining a crystalline material (hereinafter called "the Product") consisting essentially of the enantiomeric pair of isomers represented by (S)-α-cyano-3-phenoxybenzyl (1R,cis)-3-(Z-2-chloro-3,3,3-trifluoroprop-1-en-1-yl)-2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate in racemic proportions and substantially free from any other isomer of α-cyano-3-phenoxybenzyl 3-(2-chloro-3,3,3-trifluoroprop-1-en-1-yl)-2,2-dimethylcyclopropane carboxylate, which comprises the steps of:

(a) forming a solution of cyhalothrin with an organic solvent selected from lower alkanols containing up to 6 carbon atoms and liquid alkanes containing up to 8 carbon atoms, (b) cooling the solution to a temperature within the range −20° C. to +10° C. and optionally adding a quantity of crystals of the enantiomeric pair of isomers to the cooled solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and (e) optionally, if required, subjecting the crystalline material to recrystallisation.

By 'substantially free' is meant that not more than 10% by weight of the Product is represented by the combined weight of any other isomers of cyhalothrin.

Preferred alkanol solvents are ethanol, iso-propanol, butan-1-ol, butan-2-ol, pentan-1-ol, and iso-propanol/t-butanol (1:1), isopropanol/1,2-ethanediol (2:1). Isopropanol is particularly preferred. Preferred liquid alkane solvents are n-hexane and n-heptane.

By a concentrated solution is meant preferably one containing from 2:1 to 1:5, and most preferably 1:1, parts by weight of cyhalothrin:solvent.

The cyhalothrin used in this process may be contaminated with up to 10% by weight of the corresponding trans isomers and (E)-isomers. Preferably cyhalothrin of at least 95% purity is used since this usually provides the Product in higher yield and purity.

If the process is performed using a quantity of added crystals of the enantiomeric pair if isomers this usually shortens the time required to effect precipitation of the Product from the solution. (A quantity of the enantiomer pair of isomers of sufficient purity to be added may be obtained by subjecting cyhalothrin to high performance liquid chromatography (HPLC) to separate the desired enantiomeric pair of isomers from the other isomers present).

The process is preferably conducted by preparing the solution using slight warming if necessary, and then cooling the solution to a temperature in the range 0° to 10° C. for a first period during which time a substantial amount of Product crystallises, and thereafter further cooling the solution to a temperature in the range −15° to −5° C. for a second period until crystallisation is substantially complete before collecting the precipitated Product.

If recrystallisation is required to free the Product from other isomers which may have coprecipitated with the product this may be achieved by using any suitable recrystallisation solvent, for example, the solvents referred to above as useful in the process for obtaining the Product.

In practising the process repeatedly it was discovered that the Product may be precipitated in one of two different forms, hereinafter called "Product I" and "Product II". Typically Product I precipitates only slowly and the period of time required to achieve a reasonable yield is preferably at least from 7 to 15 days or even longer. Product II precipitates out much more rapidly and good yields can be achieved in a time period of from 1 to 6 days.

Where the added crystals of the enantiomeric pair of isomers were obtained by HPLC separation then the precipitate is usually in the form of Product I. If this precipitated material is recrystallised several times and then used to nucleate further crystallisations then it was noted that Product II was obtained. Product II, once obtained, when used to nucleate further crystallisations will always cause the Product to precipitate in the form of Product II.

Analysis of this material showed it to be a novel form of the Product having several advantages over Product I as can be seen from the following description of the two forms.

Product I is white crystalline material having a melting point within the range 36°–42° C. when precipitated by the above process. When freed from contamination by residual amounts of isomer C and isomer D by recrystallisation Product I melts at 41°–42° C. Infra red spectral analysis shows it to consist of a conglomerate of mixed crystals in which each individual crystal is composed of molecules of a single isomer, either isomer A or isomer B, there being approximately equal amounts of crystals of each isomer. Product I is therefore a racemic mixture. These crystals are fine needles which, as indicated above, are relatively slow to crystallise out even from concentrated solutions of cyhalothrin. Collecting the Product by filtration can also be slow due to the tendency of the fine needles to clog the filter.

Product II is characterised by having a melting point above 47° C., typically 48° to 50° C. This form crystallises out more rapidly and the crystals are rhomboid-like in shape but are in fact monoclinic. This permits easier collection by filtration since the crystals of this form do not tend to clog the filter in the manner of the needles of the lower melting form described above.

Product II is thus a more convenient form of the Product by virtue of its characteristics permitting more economic production and easier handling of the Product for use in insecticide manufacture.

Infra-red spectroscopic and X-ray crystallographic analysis of this higher melting form indicate that each individual crystal is composed of equal amounts of isomer A and isomer B arranged regularly in the crystal lattice. This form is thus a racemic compound.

Data concerning the crystalline form of Product II was collected by examining the X-ray diffraction characteristics of a crystal of dimensions ca. 0.13×0.13×0.12 mm using a Philips PW1100 four circle X-ray diffractometer with Mo-$K_\alpha$ radiation from a graphite monochromator. A $\theta$-$2\theta$ scan mode was used with a scan speed of $0.5s^{-1}$, a scan width of 0.8° and reflections with $3 \leq \theta \leq 25°$ were examined using the technique described by K. R. Adam et al, *Inorg. Chem.*, 1980, 19, 2956. The data obtained for Product II may be summarised as follows:

Crystal form: monoclinic
Space Group: C2/c
a=34.764(5), b=7.023(2), c=18.624(3) Å
$\beta$=101.95(3)°, U=4448.46 Å$^3$, Z=8
Density=1.343 g.cm$^{-3}$, F(000)=1856.
(Mo-$K_\alpha$)=1.77 cm$^{-1}$, (Mo-$K_\alpha$)=0.71069 Å

The crystal lattice consists of regularly packed alternate molecules of the two isomers A and B, each with the trifluoromethyl group trans to the cyclopropane group across the double bond (ie. the Z-configuration). The unit cell contains 4 molecules of each enantiomeric isomer.

In a further aspect, the invention provides insecticidal preparations containing the product and methods of using them to combat and control insect pests. Except for the active ingredient these preparations and methods are identical to those preparations and methods set forth in U.S. Pat. No. 4,183,948 referred to above, the disclosure of which is herein incorporated by reference.

The invention is illustrated by the following Examples.

In the Examples, isomer A is referred to as the 1R, cis-S isomer, ie. the isomer having the (R) configuration at the carbon atom of the cyclopropane ring attached to the carboxylate group, cis referring to the relationship between the two hydrogen atoms on the cyclopropane ring and having the (S) configuration at the carbon atom bearing the cyano group. Isomer B is referred to the 1S,cis-R isomer, isomer C as the 1R,cis-R and isomer D as the 1S,cis-S isomer.

Examples 1 and 2 are merely illustrative of the preparation of the racemic mixture (Product I) and do not form a part of this invention.

EXAMPLE 1

This Example illustrates the separation of α-cyano-3-phenoxybenzyl cis-3-(Z-2-chloro-3,3,3-trifluoroprop-1-en-1-yl)-2,2-dimethylcyclopropane carboxylate into its constituent pairs of enantiomeric isomers.

The material to be separated was characterised by thin layer chromatographic separation of a sample on 0.25 mm (analytical grade) silica gel plates using various eluents. There was slight separation of two components corresponding to the two pairs of enantiomers present. The mean $R_f$ values for the two components were as follows:

| Eluent<br>Diethyl ether:n-hexane | $R_f$ (average) | $\Delta R_f$ |
| --- | --- | --- |
| 10:90 | 0.22 | 0.025 |
| 15:85 | 0.28 | 0.030 |
| 20:80 | 0.33 | |

Separation of the material was achieved by use of high performance liquid chromatography using a Waters Associates System 500 apparatus fitted with a "Prep-PAK-500" silica column. This was loaded with 0.5 g of cyhalothrin consisting of a 55:45 mixture of the 1S,cis-S/1R,cis-R:1R,cis-S/1S,cis-R enantiomer pairs. The eluent was diethyl ether/petroleum ether (boiling range 40°–60° C.) mixture (1:9) and the flow rate was 0.2 liters per minute. Fractions were collected after four recycles. The first fraction was identified by proton magnetic resonance spectroscopy as the 1R,cis-R/1S,cis-S enantiomer pair and the second fraction as the 1R,cis-S/1S,cis-R enantiomer pair. Each fraction had a purity of ca. 98% and together corresponded to about 60% of the amount injected. The p.m.r. data is set out as follows ($\delta$ values in CDCl$_3$):

| 1R,cis-S/1S,cis-R | | 1S,cis-S/1R,cis-R | |
| --- | --- | --- | --- |
| 1.21 | ⎫ (d) | 1.34 | (s) |
| 1.30 | ⎭ | | |
| 1.98 | ⎫ | 1.98 | ⎫ |
| 2.07 | | 2.07 | |
| 2.19 | ⎬ (m) | 2.19 | ⎬ (m) |
| 2.29 | | 2.29 | |
| 2.38 | ⎭ | 2.38 | ⎭ |
| 6.38 | (s) | 6.32 | (s) |

-continued

| 1R,cis-S/1S,cis-R | | 1S,cis-S/1R,cis-R | |
|---|---|---|---|
| 6.77 ⎫ | | 6.77 ⎫ | |
| 6.87 ⎭ (d) | | 6.87 ⎭ (d) | |
| 6.97–7.50 | (m) | 6.97–7.50 | (m) |

EXAMPLE 2

This Example illustrates the crystallisation of the 1R,cis-S/1S,cis-R enantiomer pair from a solution of cyhalothrin. The crystals used for seeding were obtained by the process of Example 1 above.

455.6 g of a mixture of cis-isomers of α-cyano-3-phenoxybenzyl 3-(Z-2-chloro-3,3,3-trifluoroprop-1-en-1-yl)-2,2-dimethylcyclopropane carboxylate, containing 43.2% by weight of the 1R,cis-S and 1S,cis-R isomers and 56.8% by weight of the 1S,cis-S and 1R,cis-R isomers was dissolved in 460 ml of isopropanol that had been previously dried by distillation from calcium hydride. Dissolution was effected by warming the mixture to approximately 50° C. The solution was cooled to 3° C. whilst stirring with a polytetrafluoroethylene coated magnet, then seeded with a few crystals of a mixture of 1R,cis-S and 1S,cis-R isomers of α-cyano-3-phenoxybenzyl 3-(Z-2-chloro-3,3,3-trifluoroprop-1-en-1yl)-2,2-dimethylcyclopropane carboxylate. Stirring was continued at that temperature for 9 days then the suspension cooled to −10° C. and stirred vigorously with a polytetrafluoroethylene paddle for 7 days.

The solid which had separated out was filtered off at 3° C., sucked dry, washed once with 100 ml of 40°–60° petroleum ether at 3° C. and dried to constant weight in a vacuum dessicator over phosphorus pentoxide to give 97.6 g of white crystals. This product was shown by capillary gas liquid chromatography to contain 86.9% by weight of a 1:1 mixture of the 1R,cis-S and 1S,cis-R isomers of the starting material. The solid was dissolved in 300 ml of dry 40°–50° petroleum ether, the solution cooled to 3° C. with stirring and a few crystals of a mixture of 1R,cis-S and 1S,cis-R isomers of α-cyano-3-phenoxybenzyl 3-(Z-2-chloro-3,3,3-trifluoroprop-1-en-1-yl)-2,2-dimethylcyclopropane carboxylate, added as seed. After 2 hours the resultant white suspension was filtered at 3° C. and the solid sucked dry. Further drying in a vacuum dessicator over phosphorus pentoxide gave 73.6 g of a white solid containing 92% by weight of a mixture of the 1R,cis-S and 1S,cis-R isomers of α-cyano-3-phenoxybenzyl3-(Z-2-chloro-3,3,3-trifluoroprop-1-en-1-yl)-2,2-dimethylcyclopropane carboxylate, melting in the range 36°–42° C.

EXAMPLE 3

A mixture of cyhalothrin isomers consisting of 6.4 g of the 1R,cis-S isomer, 6.4 g of the 1S,-cis-R isomer, 3.2 g of the 1S,cis-S isomer and 3.2 g of the 1R,cis-R isomer was dissolved in n-hexane (20 ml) and stirred under a nitrogen atmosphere whilst maintaining the temperature at −5° C. After dissolution and cooling a few milligrams of the racemic mixture (obtained by the process of Example 2 and further purified by recrystallisation until the melting point was 41.5°–42.0° C.) was added and the stirring continued for 16 hours at −5° C. The precipitated solid was collected by filtration on a sintered glass funnel cooled to 0° C. and washed twice with hexane cooled to −5° C. There was thus obtained 9.30 g of a material m.p. 48°–49.5° C. having a purity of at least 99% with respect to cyhalothrin isomers and consisting of at least 96.3% of the 1R,cis-S and 1S,-cis-R isomers in equal proportions.

Infra red analysis indicates it to be different from the product of Example 2. The crystalline form is also different (rhomboid rather than needles) and this together with the higher melting point indicates it to be the racemic compound in which individual crystals contain equal amounts of the 1R,cis-S and 1S,cis-R isomers, both molecules being disposed in a regular arrangement throughout the crystal lattice.

Infra red (liquid paraffin mull): 1050, 1030, 1010, 990, 970 (shoulder) 963, 950, 935, 920, 908, 904, 895, 888, 873, 838, 830 (shoulder) 820, 805, 795, 785, 760, 748, 725, 702, 695, 650 cm$^{-1}$.

Figure 2:
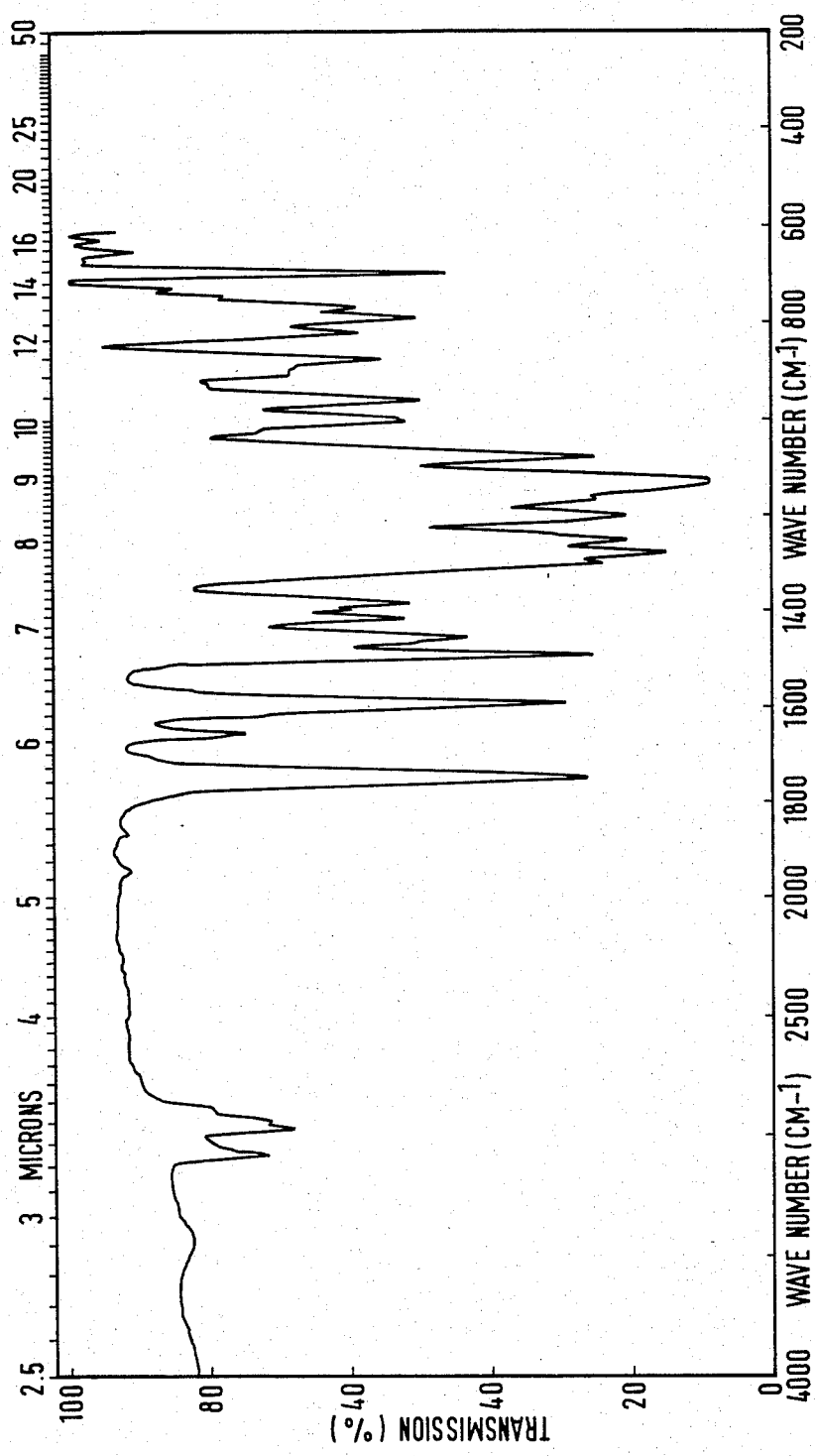
Figure 3:
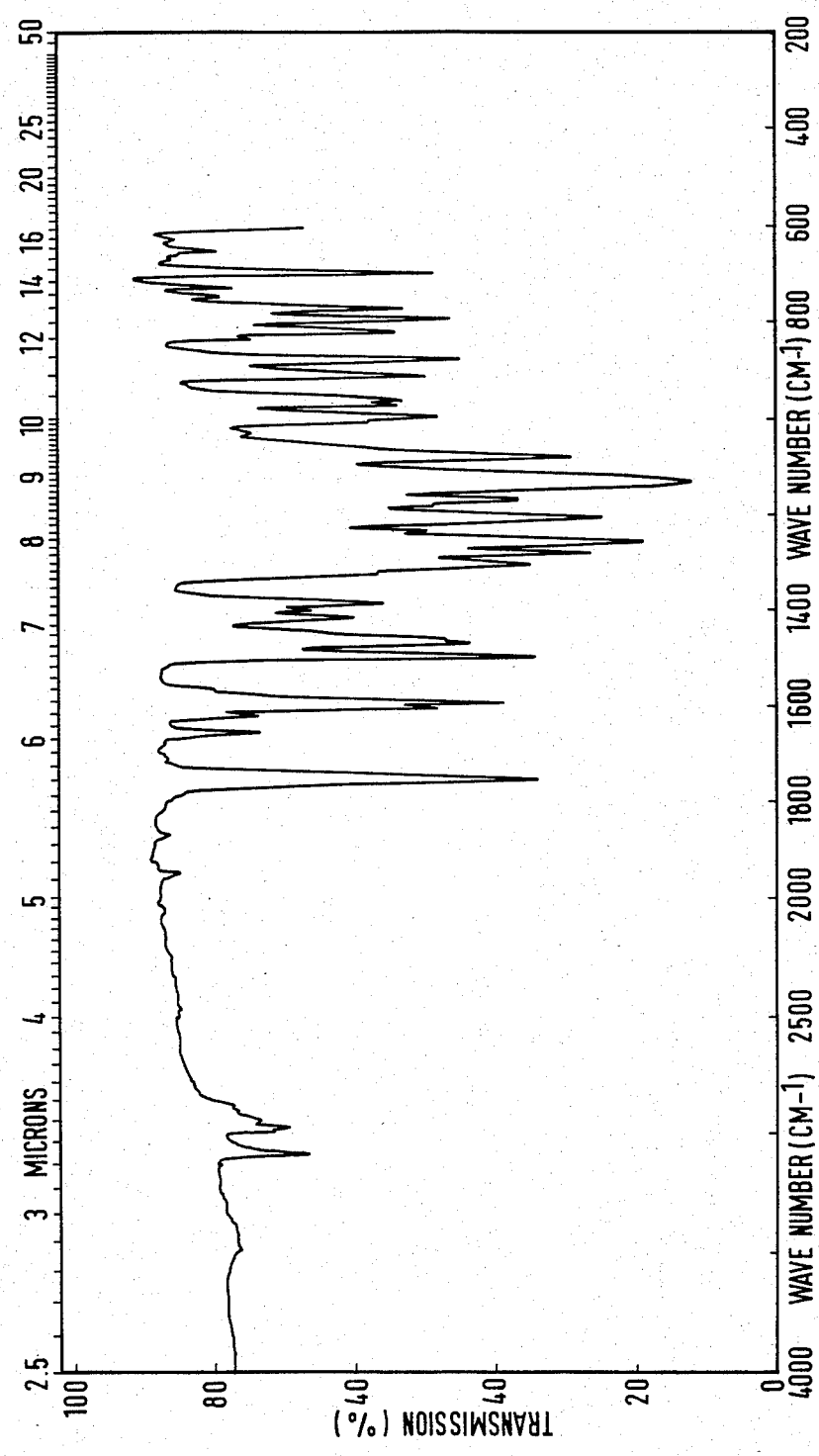

FIGS. 1 and 2 show the infra red spectra for the product of this Example and that of the product of Example 2 respectively. FIG. 3 shows the infra red spectrum for the 1R,cis-S isomer alone. It can be seen that the spectrum for the product of Example 2 and that of the 1R,cis-S isomer alone are identical, indicating that the product of Example 2 is a conglomerate or racemic mixture, whereas the different spectrum for the product of Example 3 indicates it to be the racemic compound.

EXAMPLE 4

A mixture of cyhalothrin isomers consisting of 20.61 g of isomer A, 20.61 g of isomer B, 4.04 g of isomer C and 4.04 g of isomer D was dissolved in warm hexane (100 ml), cooled to 5° C. and a small quantity of the Product of Example 3 added. The mixture was then cooled slowly to −5° C. with vigorously agitation.

The precipitate was collected by filtration, washed on the filter with cold hexane and air dried, to yield the racemic compound of the 1R,cis-S and 1S,cis-R isomers, (28.6 g) m.p. 49°–50° C.

EXAMPLE 5

This Example illustrates the precipitation of the racemic compound form of the Product (Product II). A mixture of technical cyhalothrin (200 g, purity 95.8% by weight) and isopropanol (200 ml) was charged to a round bottomed glass flask containing a number of glass beads, cooled to −5° C. and crystals of the racemic compound (4.0 g) added. The cooled mixture was agitated for 23 hours at −5° C. by rotating the flask. The precipitate was collected by slurrying the mixture into a precooled jacketted sinter kept at −5° C. and the filter cake washed by slurrying with precooled n-hexane (one bed volume) to yield (after drying) the racemic compound consisting of the 1R,cis-S and 1S,cis-R isomers of cyhalothrin, (39.5 g), melting point 49.5°–50° C.

I claim:

1. The enantiomeric pair of isomers represented by (S)-α-cyano-3-phenoxybenzyl 1R,cis-3-(Z-2-chloro-3,3,3-trifluoroprop-1-en-1-yl)-2,2-dimethylcyclopropane carboxylate and (R)-α-cyano-3-phenoxybenzyl 1S,cis-3-(Z-2-chloro-3,3,3-trifluoroprop-1-en-yl)-2,2-dimethylcyclopropane carboxylate in racemic proportions and substantially free from any other isomer of α-cyano-3-phenoxybenzyl 3-(2-chloro-3,3,3-trifluoroprop-1-en-1-yl)-2,2-dimethylcyclopropane carboxylate in crystalline form having a melting point greater than 47° C.

2. The enantiomeric pair of isomers according to claim 1 having melting point within the range 48°–50° C.

3. A crystalline material consisting essentially of the enantiomeric pair of isomers according to claim 1 in the form of the racemic compound of the isomers characterised in that the infra-red absorption spectrum is distinguishable from that of either of the isomers in crystalline form in isolation.

4. The crystalline form of the enantiomeric pair of isomers according to claim 3 in which the crystal lattice has the following characteristics:

Space group C2/c, a=34.764(5) Å, b=7.023(2) Å c=18.624(3) Å, $\beta$=101.95(3)°, $\mu$=4448.46 Å, Z=8.

5. The enantiomeric pair of isomers according to claim 3 in the form of crystals of monoclinic form having a density of 1.343 g.cm$^{-1}$.

* * * * *